United States Patent [19]

Horodysky et al.

[11] Patent Number: 4,522,629
[45] Date of Patent: Jun. 11, 1985

[54] BORATED PHOSPHONATES AS LUBRICANT AND FUEL ADDITIVES

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 535,131

[22] Filed: Sep. 23, 1983

[51] Int. Cl.$^3$ .................................................. C10L 1/30
[52] U.S. Cl. ............................................ 44/53; 44/56; 44/57; 44/76; 252/403; 252/49.9; 260/922
[58] Field of Search ................... 44/53, 56, 57, 76; 252/403; 260/922

[56] References Cited

U.S. PATENT DOCUMENTS

| | | | |
|---|---|---|---|
| 3,325,261 | 6/1967 | Knowles et al. | 44/72 |
| 3,505,044 | 4/1970 | Bartlett et al. | 44/76 |
| 4,416,667 | 11/1983 | Kaufman et al. | 44/53 |
| 4,440,656 | 4/1984 | Horodysky | 44/76 |

Primary Examiner—Y. Harris-Smith
Attorney, Agent, or Firm—Alexander J. McKillop; Michael G. Gilman; Claude E. Setliff

[57] ABSTRACT

Compounds made by reacting a vicinal diol with a hydrocarbyl phosphite and then borating the resulting product have been found to be effective friction reducers when added to lubricants or fuels. This is true in any use of lubricants, but is especially true when they are used in internal combustion engines. In the latter case, the fuels used, when they contain the additive, aid in the reduction of friction in the engine.

26 Claims, No Drawings

BORATED PHOSPHONATES AS LUBRICANT AND FUEL ADDITIVES

BACKGROUND OF THE INVENTION

1. Field of the Invention

The invention relates to lubricant and liquid fuel compositions. In particular, it relates to the use of borated derivatives of the product of reaction between hydrocarbyl vicinal diols and dihydrocarbyl phosphites.

2. Discussion of the Prior Practices and Disclosures

Alcohols are well known for their lubricity properties when formulated into lubricating oils and for their water-scavenging characteristics when blended into fuels. The use of vicinal hydroxyl-containing alkyl carboxylates such as glycerol monooleate have also been used widely as lubricity additives. U.S. Pat. No. 2,788,326 discloses some of the esters suitable for the present invention, e.g., glycerol monooleate, as minor components of lubricating oil compositions.

Certain phosphorus compounds are known for their use in lubricants. The closest compounds known are dihydrocarbyl hydrocarbylphosphonates disclosed in U.S. Pat. No. 4,356,097. No patents or other publications are known that teach or suggest the borates of the present invention.

SUMMARY OF THE INVENTION

In accordance with the invention, there is provided a major proportion of a liquid fuel or lubricant composition comprising fuel or lubricant and a friction reducing amount of a borated product of reaction obtained by reacting a hydrocarbyl vicinal diol, a dihydrocarbyl phosphite and a boron-containing compound. "Hydrocarbyl" is a group containing 10 to 30 carbon atoms in the case of the vicinal diol and 1 to 30 carbon atoms in the case of the phosphite, and embraces alkyl, alkenyl, aryl, alkaryl, aralkyl and cycloalkyl groups, preferably alkyl groups. The borated products have significantly greater friction reducing properties, higher viscosity indices, and good low temperature characteristics and solubility characteristics when used in low additive concentrations.

BACKGROUND OF THE INVENTION

It has now been found that the borated products of this invention significantly improve friction reducing properties and impart an antioxidant component to fuels and lubricants. In addition to the friction reducing properties described, the borated esters possess much improved solubility characteristics, especially in synthetic fluids, over those of the non-borated derivatives. These phosphorus- and boron-containing compounds are non-corrosive to copper, possess antioxidant and potential antifatigue characteristics and exhibit antiwear and high temperature dropping point properties for greases.

The hydrocarbyl vicinal diols contemplated for use in this invention are hydrocarbyl diols having vicinal hydroxyl groups. Preferred are the aliphatic members, and more preferably the alkyl members. They have the formula:

R(OH)$_2$ wherein R is a hydrocarbyl group containing 10 to 30 carbon atoms. R can be linear or branched, saturated or unsaturated, with linear saturated members being preferred to maximize friction reduction. The two hydroxyl groups can be on any adjacent carbon atoms along the hydrocarbyl chain, but the terminal diols are much preferred. R includes, but is not limited to decyl, dodecyl, tetradecyl, pentadecyl, hexadecyl, heptadecyl, octadecyl, eicosyl and the like, and mixtures of such hydrocarbyl groups. Included are mixtures of $C_{15}$ to $C_{18}$ alcohols, $C_{14}$ to $C_{16}$ alcohols and $C_{20}$ to $C_{24}$ alcohols.

The vicinal diols can be synthesized using several methods known to the art, such as one described in *J. Am. Chem. Soc.*, 68, 1504 (1946). The method described involves the hydroxylation of 1-olefins with peracids. Vicinal diols can also be prepared by the peroxytrifluoroacetic acid method for the hydroxylation of olefins as described in *J. Am. Chem. Soc.*, 76, 3472 (1954). Similar procedures can be found in U.S. Pat. Nos. 2,411,762, 2,457,329, 2,455,892.

The diols can also be prepared via catalytic epoxidation of an appropriate olefin followed by hydrolysis to form the appropriate vicinal diol.

The preferred vicinal diols contain 12 to 20 carbon atoms. Below a carbon number of 12, friction reducing properties are significantly reduced. Above a carbon number of 20, solubility constraints may become significant for fluid lubricant. More preferred are the $C_{14}$ to $C_{17}$ hydrocarbyl groups in which solubility, frictional characteristics and other properties are maximized. For greases, however, carbon numbers up to 30 are preferred.

Among the diols contemplated for reaction with the boron compound are 1,2-decanediol, 1,2-dodecanediol, 1,2-tetradecanediol, 1,2-pentadecanediol, 1,2-hexadecanediol, 1,2-octadecanediol, 1,2-mixed $C_{15}$ to $C_{18}$-alkanediols and mixtures of any two or more of these.

The dihydrocarbyl phosphite that may be used in the practice of this invention is one coming within the formula

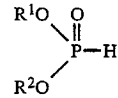

wherein $R^1$ is a hydrocarbyl group containing 1 to 30, preferably 1 to 6 carbon atoms and $R^2$ is a hydrocarbyl group containing 1 to 6 carbon atoms. $R^1$ may be an alkyl, alkenyl, aryl, aralkyl, alkaryl or cycloalkyl group, preferably an alkyl group such as a methyl, ethyl, butyl, hexyl, octyl, decyl, tetradecyl, octadecyl, eicosyl or triacontyl group. It may be an ethenyl, butenyl, octenyl or oleyl group. $R^2$ may also be an alkyl, alkaryl, or $C_6$ aryl group, including methyl, ethyl, propyl, butyl, pentyl, hexyl, the unsaturated members thereof, and phenyl. Preferably the unsaturated members contain only double bonds. Examples of useful phosphites are the dimethyl, diethyl, dibutyl, methylethyl, hexyl, tetradecyl, phosphites, and the like.

The phosphites employed in this invention can be made using a single diol or mixtures of two or more diols. Such mixtures can contain from about 5% to about 95% by weight of any one constituent, the other constituent(s) being selected such that it or they together comprise from about 95% to about 5% by weight of the mixture. Mixtures are often preferred to the single-member component. The phosphite reaction can be performed at about 70° C. to about 250° C., with about 100° C. to about 160° C. being preferred. Less than a stoichiometric amount of phosphite can be used and is often preferred to a stoichiometric amount.

Reaction times can be from about 1 hour to about 24 hours.

The useful boron compounds include boric oxide, metaborates and others, such as those of the formula $$(R^3O)_xB(OH)_y$$

where $R^3$ is a $C_1$ to $C_6$ alkyl group, x is 0 to 3 and y is 0 to 3, the sum of x and y being 3. The borates embraced include mono-, di- and trimethyl borate, mono-, di- and triethyl borate, mono-, di- and tripropyl borate, mono-, di- and tributyl borate, mono-, di- and triamyl borate and mono-, di- and trihexyl borate. Combinations of these, including combinations of trialkyl borates and boric acid, can be used as the borating agent.

Overall reaction temperatures of 90° C. to 260° C. or more can be used for boration, but 110° to 200° C. is preferred. Preferred reaction temperatures for boration with the trialkyl borate will range from about 180° C. to about 260° C. Reaction times can be from 1 to 24 hours and more.

The product of reaction can be made by (1) reacting the hydrocarbyl vicinal diol with a dihydrocarbyl phosphite and (2) reacting the product thus formed with a boron-containing compound. In this reaction, boron concentration can be less than stiochiometric, stoichiometric or in excess of the product of (1) to produce a derivative containing from about 0.1% to about 10% by weight of boron. At least 5 to 10% of the available hydroxyl groups should be borated to derive substantial beneficial effect, but a stoichiometric excess of boron compound up to a 10% excess (more than an equivalent amount of borating agent compared to available hydroxyl groups) can also be charged to the reaction medium, resulting in a product containing the maximum stated amount of boron. A stoichiometric excess of boron is occasionally desirable, especially for solid lubricant applications.

The reaction product can also be made by (1) reacting a boron compound with a diol, followed by (2) reacting the borated diol with the phosphite. In the reaction in which diol and phosphite are first reacted, one may, as noted, use less than a stoichiometric amount of boron. The reaction in which boron is first reacted with the diol must use less than a stiochiometric amount of boron. Otherwise, no hydroxyl groups would remain for reaction with the phosphite. As in the former reaction, enough boron should be reacted with the diol to give a boron content in the final product of from about 0.1% to about 10% by weight. Again, at least 5% to 10% of the available hydroxyl groups should be borated, but in no case should there be less than about 5% of the diol hydroxyl groups available for reaction with the phosphite.

The borated esters are used with lubricating oils to the extent of from about 0.1% to about 10% by weight of the total composition. Also, other additives, such as detergents, antioxidants, antiwear agents viscosity index improvers, pour point depressants, dispersants, and the like may be present. These can include calcium or magnesium phenates, calcium or magnesium sulfonates, polymeric succinimides, zinc dialkyl dithiophosphates, polymers, calcium and magnesium salts and the like. Also included are di- and trisulfides, sulfurized olefins, dithionyl disulfides and the like. Preferred formulations include zinc dialkyl or diaryl dithiophosphates for maximum high temperature stabilizing properties when used with the products of this invention.

The lubricants contemplated for use with the esters herein disclosed include mineral and synthetic hydrocarbon oils of lubricating viscosity, mixtures of mineral oils and synthetic oils and greases from any of these, including mixtures. The synthetic hydrocarbon oils include long-chain alkanes such as cetanes and olefin polymers such as oligomers of hexane, octene, decene, and dodecene, etc. The mixtures of the invention are especially effective in synthetic oils formulated using mixtures of synthetic hydrocarbon olefin oligomers and lesser amounts of hydrocarbyl carboxylates ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acid having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids, fatty esters, fatty glycerides and fatty materials having from about 12 to about 30 carbon atoms per molecule, including the metal salts of hydroxyl-containing fatty acids, fatty esters and fatty glycerides. Examples of useful thickeners within these classes are 12-hydroxystearic acid and the esters and glycerides thereof. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylateacetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydro-phobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15, percent by weight of the total grease composition.

The liquid fuels contemplated include liquid hydrocarbon fuels such as fuel oils, diesel oils and gasolines and alcohol fuels such as methanol and ethanol or mixtures of these fuels. The additives of the invention are useful therein over the range of from about 5 to about 250 lbs. per 1000 bbls. of fuel.

In both reactions described hereinabove, a solvent is preferred. Solvents that can used include the hydrocarbon solvents, such as toluene, benzene, xylene, and the like (for the diol-phosphite reaction), alcohol solvents such as propanol, butanol, pentanol and the like, as well as mixtures of hydrocarbon solvents or alcohol solvents and mixtures of hydrocarbon and alcohol solvents (for the boration reaction).

Having described the invention in general terms, the following are offered to specifically illustrate the development. It is to be understood they are illustrations only and that the invention shall not be limited except as limited by the appended claims.

EXAMPLE 1

1,2-Mixed Pentadecanediol-Octadecanediol Derived Hydrogen Phosphite (3:1)

Approximately 360 g of 1,2-mixed pentadecanediol to octadecanediol (commercially obtained as Vikol 158 from Viking Chemical Co. and containing about 28% 1,2-pentadecanediol, about 28% 1,2-hexadecanediol, about 28% 1,2-heptadecanediol and about 16% octadecanediol, all percentages by weight) were charged to a glass reactor equipped with heater, agitator, Dean-Stark tube with condenser and provision for blanketing the vapor space with nitrogen. The contents were heated to 70° C. to liquify the solids and 55 g of dimethyl phosphite were slowly added. The reaction mixture was heated to 110° C. and held for 2 hours, held at 120° C. for 1 hour and held at 130° C. for 1 hour. Methanol was observed forming and collecting in the trap. The crude product was vacuum stripped at 150° C. to remove volatile materials, producing 375 g of intermediate additive. The intermediate was an amber fluid which became waxy after cooling.

EXAMPLE 2

Partially Borated 1,2-Pentadecanediol-Octadecanediol Derived Partial Hydrogen Phosphite Approximately 135 g of the phosphorus-containing product of Example 1, 100 g of toluene and 7 g of boric acid were charged to a reactor equipped as described in Example 1. The reactor contents were heated to 155° C. over a period of 4½ hours during which time water evolution, as a result of azeotropic distillation, ceased. The solvent was removed by vacuum distillation at 160° C. The product was cooled to 120° C. and filtered through diatomaceous earth. The product was an amber fluid which became waxy after cooling.

EXAMPLE 3

Borated 1,2-pentadecanediol-Octadecanediol Derived Partial Hydrogen Phospite

Approximately 135 g of the phosphorus containing product of Example 1, 100 g toluene and 14 g of boric acid were charged to a reactor equipped as described in Example 1. The reactor contents were heated to 155° C. over a period of 5 hours during which time water evolution, as a result of azeotropic distillation, ceased. The solvent was removed by vacuum distillation at 160° C. The product was cooled to 120° C. and filtered through diatomaceous earth to yield an amber fluid which became waxy after further cooling.

EXAMPLE 4

1.2-Mixed Pentadecanediol-Octadecanediol Derived Hydrogen Phosphite (2:1)

Approximately 480 g of 1,2-mixed pentadecanediol to octadecanediol of Example 1 were charged to a glass reactor equipped as generally described in Example 1. The contents were heated to about 65° C. and 100 g of dimethyl phosphite were slowly added. The reaction mixture was heated to 110° C. and held for 2 hours, held at 120° C. for 1 hour and held at 130° C. for 1 hour. Methanol was observed forming and collecting in the trap during this period. The temperature was raised to 150° C. and the intermediate was vacuum topped to remove volatile materials. The intermediate was an amber fluid which became waxy after cooling.

EXAMPLE 5

Borated 1,2-Pentadecanediol-Octadecanediol Derived Partial Hydrogen Phosphite

Approximately 120 g of the phosphorus containing product of Example 4, 100 g of toluene and 11 g of boric acid were charged to a reactor equipped as described in Example 1. The reactor contents were heated to 150° C. over a period of 4 hours until water evolution during azeotropic distillation ceased. The solvent was removed by vacuum distillation at 150° C. The product was cooled to 120° C. and filtered through diatomaceous earth to yield an amber fluid which became waxy after further cooling.

EXAMPLE 6

1,2-Dodecanediol Derived Hydrogen Phosphite (2:1)

Approximately 200 g of 1,2-dodecanediol were charged to a reactor equipped as generally described in Example 1. The contents were warmed to about 60° C. and 55 g of dimethyl phosphite were slowly added. The reaction mixture was heated at 110° C. for 2 hours, 120°

C. for 1 hour and 130° C. for 1 hour. Methanol was observed forming and collecting in the trap during this reaction period. The temperature was raised to 145° C. and the intermediate was vacuum topped. Approximately 222 g of amber fluid were recovered and became waxy after cooling.

EXAMPLE 7

Approximately 113 g of the phosphorus containing product of Example 6, 100 g of toluene and 11 g of boric acid were changed to a reactor equipped as described in Example 1. The reactor contents were heated to 155° C. over a period of 6 hours until water evolution during azeotropic distillation ceased. The solvent was removed by vacuum distillation at 155° C. The product was cooled to 110° C. and filtered through diatomaceous earth. The product was an amber fluid which became waxy after cooling.

EVALUATION OF PRODUCTS

The borated hydrocarbyl diol derived phosphites were blended into fully formulated synthetic and mineral oil-based engine oil lubricants and evaluated using the Low Velocity Friction Apparatus Test. The formulations include polymeric dispersants, metallic phenates and sulfonates, zinc dialkyl dithiophosphates and polymeric viscosity index improving additives. The use of only ½% of the product of Example 2 reduced the coefficient of friction by 52% as shown in Table 1. These compositions appear to be exceptionally concentration effective reducers.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force leading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches.

The data obtained are shown in Table 1. The data in Table 1 are reported as percent reduction in coefficient of friction at two speeds. The friction-reducing ester additives were elevated in a fully formulated 5W-30 synthetic lubricating oil comprising an additive package including anti-oxidant, detergent and dispersant. The oil had the following general characteristics:

Viscosity 100° C.—11.0 cs
Viscosity 40° C.—58.2 cs
Viscosity Index—172

TABLE 1

| Composition | Additive Conc. Wt. % | % Reduction in Coefficient of Friction in LVFA at | |
|---|---|---|---|
| | | 5 Ft./Min. | 30 Ft./Min. |
| Base Oil-SAE 5W-30 fully formulated synthetic engine oil | — | 0 | 0 |
| Example 2 Plus Base Oil | 0.5 | 52 | 43 |
| Example 3 Plus Base Oil | 0.5 | 29 | 29 |

TABLE 2

| Composition | Additive Conc. Wt. % | % Reduction in Coefficient of Friction in LVFA at | |
|---|---|---|---|
| | | 5 Ft./Min. | 30 Ft./Min. |
| Base Oil-SAE 10W-40 fully formulated mineral oil | — | 0 | 0 |
| Example 2 Plus Base Oil | 1 | 33 | 26 |
| Example 3 Plus Base Oil | 1 | 33 | 32 |
| Example 5 Plus Base Oil | 1 | 29 | 29 |

We claim:

1. A product of reaction made by reacting a hydrocarbyl vicinal diol containing 10 to 30 carbon atoms, a dihydrocarbyl phosphite of the formula

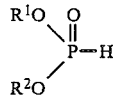

wherein R is a hydrocarbyl group containing 1 to 30 carbon atoms and $R^2$ is a hydrocarbyl group containing 1 to 6 carbon atoms and a boron compound, the reaction being run at from about 70° C. to about 260° C. using amounts of reactants such that in the final product at least about 5% of the hydroxy groups originally available are borated.

2. The product of claim 1 wherein $R^1$ is an alkyl, alkenyl, aryl, aralkyl, alkaryl or cycloalkyl group.

3. The product of claim 1 wherein $R^2$ is an alkyl, a six carbon aryl or aryl group.

4. The product of claim 2 wherein $R^1$ is a methyl, ethyl, butyl, hexyl, octyl, decyl, tetradecyl, octadecyl, eicosyl, triacontyl, ethylene, butylene, octenyl or oleyl group.

5. The product of claim 3 wherein $R^2$ is selected from the group consisting of methyl, ethyl, propyl, butyl, pentyl, hexyl, the saturated members thereof and phenyl.

6. The product of claim 1 wherein the boron compound is boric oxide, a metaborate or is of the formula $$(R^3O)_xB(OH)_y$$

wherein $R^3$ is a $C_1$ to $C_6$ alkyl group, x is 0 to 3 and y is 0 to 3, the sum of x and y being 3.

7. The product of claim 6 wherein the boron compound is boric acid.

8. The product of claim 6 wherein the boron compound is mono-, di- or trimethyl borate, mono-, di- or triethyl borate, mono-, di or tripropyl borate, mono-, di- or tributyl borate, mono-, di-, or triamyl borate or mono-, di- or trihexyl borate.

9. The product of claim 1 wherein the vicinal diol is 1,2-mixed $C_{15}$ to $C_{18}$ alkanediols.

10. The product of claim 1 wherein the vicinal diol is a $C_{12}$ diol.

11. The product of claim 9 wherein the vicinal diol is 1,2-mixed $C_{15}$ to $C_{18}$alkane diols, the phosphite is dimethyl phosphite and the boron compound is boric acid.

12. The product of claim 10 wherein the vicinal diol is 1,2-dodecanediol, the phosphite is dimethyl phosphite and the boron compound is boric acid.

13. A liquid fuel composition comprising a major proportion of a liquid fuel and from about 5 to about 250 pounds per 1000 barrels of said liquid fuel of a reaction product made by reacting a hydrocarbyl vicinal diol containing 10 to 30 carbon atoms, a dihydrocarbyl phosphite of the formula

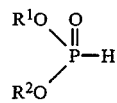

wherein R is a hydrocarbyl group containing 1 to 30 carbon atoms and $R^2$ is a hydrocarbyl group containing 1 to 6 carbon atoms and a boron compound, the reaction being run at from about 70° C. to about 260° C. using amounts of reactants such that in the final product at least about 5% of the hydroxy groups originally available are borated.

14. The composition of claim 13 wherein $R^1$ is an alkyl, alkenyl, aryl, aralkyl, alkaryl or cycloalkyl group.

15. The composition of claim 13 wherein $R^2$ is an alkyl, aryl or aryl a six carbon group.

16. The composition of claim 14 wherein $R^1$ is a methyl, ethyl, butyl, hexyl, octyl, decyl, tetradecyl, octadecyl, eicosyl, triacontyl, ethylene, butylene, octenyl or oleyl group.

17. The composition of claim 15 wherein $R^2$ is selected from the group consisting of methyl, ethyl, propyl, butyl, pentyl, hexyl, the saturated members thereof and phenyl.

18. The composition of claim 13 wherein the boron compound is boric oxide, a metaborate or is of the formula

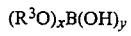

wherein $R^3$ is a $C_1$ to $C_6$ alkyl group, x is 0 to 3 and y is 0 to 3, the sum of x and y being 3.

19. The composition of claim 18 wherein the boron compound is boric acid.

20. The composition of claim 18 wherein the boron compound is mono-, di- or trimethyl borate, mono-, di- or triethyl borate, mono-, di or tripropyl borate, mono-, di- or tributyl borate, mono-, di-, triamyl borate or mono-, di- or trihexyl borate.

21. The composition of claim 13 wherein the vicinal diol is 1,2-mixed $C_{15}$ to $C_{18}$ alkanediols.

22. The composition of claim 13 wherein the vicinal diol is a $C_{12}$ diol.

23. The composition of claim 21 wherein the vicinal diol is 1,2-mixed $C_{15}$ to $C_{18}$-alkane diols diol-octadecane diol, the phosphite is dimethyl phosphite and the boron compound is boric acid.

24. The composition of claim 22 wherein the vicinal diol is 1,2-dodecanediol, the phosphite is dimethyl phosphite and the boron compound is boric acid.

25. The composition of claim 13 wherein the fuel is a liquid hydrocarbon fuel of a liquid alcohol fuel.

26. A method for reducing fuel consumption in an internal combustion engine by fueling said enging with a liquid fuel composition comprising a major proportion of liquid fuel and from about 5 to about 250 pounds per thousand barrels of said liquid fuel of a product of reaction made by reacting a hydrocarbyl vicinal diol containing 10 to 30 carbon atoms, a dihydrocarbyl phosphite of the formula

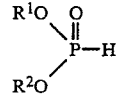

wherein $R^1$ is a hydrocarbyl group containing 1 to 30 carbon atoms and $R^2$ is a hydrocarbyl group containing 1 to 6 carbon atoms and a boron compound, the reaction to make the product being run at from about 70° C. to about 260° C. using amounts of reactants such that in the final product at least about 5% of the hydroxy group originally available are borated.

* * * * *

UNITED STATES PATENT AND TRADEMARK OFFICE
CERTIFICATE OF CORRECTION

PATENT NO. : 4,522,629

DATED : June 11, 1985

INVENTOR(S) : Andrew G. Horodysky et al

It is certified that error appears in the above-identified patent and that said Letters Patent is hereby corrected as shown below:

Column 9, line 46 (claim 15), change "aryl a six carbon group" to read -- a six carbon aryl group --.

Column 10, line 23 (claim 23), after "diols" delete "diol-octadecane diol".

Signed and Sealed this

Twenty-ninth Day of October 1985

[SEAL]

Attest:

DONALD J. QUIGG

Attesting Officer

Commissioner of Patents and Trademarks—Designate